US 6,665,565 B1

(12) United States Patent
Stomberg et al.

(10) Patent No.: US 6,665,565 B1
(45) Date of Patent: Dec. 16, 2003

(54) METHOD AND A SYSTEM FOR CONDUCTING FAILURE MODE RECOVERY IN AN IMPLANTED MEDICAL DEVICE

(75) Inventors: Charles R. Stomberg, Forest Lake, MN (US); Jean K. Ringold, Ramsey, MN (US); Ronald A. Stauffer, Princeton, MN (US)

(73) Assignee: Medtronic, Inc., Minneapolis, MN (US)

( * ) Notice: Subject to any disclaimer, the term of this patent is extended or adjusted under 35 U.S.C. 154(b) by 275 days.

(21) Appl. No.: 09/731,222

(22) Filed: Dec. 6, 2000

Related U.S. Application Data (60) Provisional application No. 60/173,081, filed on Dec. 24, 1999.

(51) Int. Cl.[7] ............................................. A61N 1/362
(52) U.S. Cl. ........................................................ 607/31
(58) Field of Search ............................... 607/30–32, 59, 607/60; 128/903, 904, 899

(56) References Cited

U.S. PATENT DOCUMENTS 5,456,692 A * 10/1995 Smith et al. ................. 607/31
5,792,204 A * 8/1998 Snell ........................... 607/32
6,198,971 B1 * 3/2001 Leysieffer .................... 607/55

* cited by examiner

Primary Examiner—George R. Evanisko
(74) Attorney, Agent, or Firm—Girma Wolde-Michael; Daniel G. Chapik; Paul H. McDowall (57) ABSTRACT

A method and a system for conducting failure mode recovery of an implanted medical device. The embodiments described reduce the risk of leaving an IMD in an undesirable state when conditions during programming of the IMD unexpectedly change. In an example embodiment, failure mode recovery in an implanted device is facilitated when a communications link with a medical communications system having an application program is interrupted. The failure mode recovery method includes establishing a communications link between the medical communications system and an extender module configured to receive an application proxy from the application program. An application proxy is then loaded into the extender module via the application program. The application proxy is configured to transition the implanted device to a recovery state in response to a set of conditions. The implanted device then transitions to a completed state via the application program, while transitioning of the completed state is monitored. The implanted device is automatically restored by the application proxy to the recovery state when the set of conditions is detected while transitioning to the completed state.

24 Claims, 4 Drawing Sheets

METHOD AND A SYSTEM FOR CONDUCTING FAILURE MODE RECOVERY IN AN IMPLANTED MEDICAL DEVICE

RELATED PATENT DOCUMENTS

This application claims priority of U.S. Provisional Application Ser. No. 60/173,081, filed on Dec. 24, 1999 (P-8745.00), entitled "Application Proxy for Telecommunication-Enabled Remote Medical Devices Access Instruments." The disclosure and drawings of the Provisional Application are specifically incorporated herein by reference.

FIELD OF THE INVENTION

The present invention generally relates to medical devices. Specifically, the invention relates to a method and a system for monitoring the reliability and integrity of a remote communication link between a programming unit and an implanted medical device.

BACKGROUND OF THE INVENTION

In recent years, implantable electronic device technology has rapidly advanced. Sizes and weights have decreased, while functionality has increased. These advances have created a corresponding demand for two-way communication or telemetry between the implantable medical device and an external device, for example, a programmer device. In a pacemaker system, for example, a programmer device downloads to an implanted pacemaker data such as operating parameters. Likewise, data may flow from the implanted device to the programmer device. Modern pacemakers are capable of storing significant amounts of data about the patient, for example, the average heart rate, and information pertaining to the pacemaker itself, for example, battery voltage level. This data may need to be transmitted to the programmer device for evaluation by a physician.

Currently implanted medical device programmers typically include an extendible head portion that includes an antenna. The antenna is connected to other circuitry in the programmer device via a stretchable coil cable. Thus, the head portion can be positioned over the patient's implanted device site for programming or telemetry interrogation of the implanted device. Command instructions or data that are downloaded to the implanted device are referred to as downlink transmissions, and data transmitted from the implanted device to the programmer device are referred to as uplink transmissions.

A technology-based health care system that fully integrates the technical and social aspects of patient care and therapy should be able to flawlessly connect the patient with care providers irrespective of separation distance or location of the participants. While clinicians will continue to treat patients in accordance with accepted modem medical practice, developments in communications technology are making it ever more possible to provide medical services in a time and place independent manner.

Prior art methods of clinical services are generally limited to in-hospital operations. For example, if a physician needs to review the performance parameters of an implanted device, the patient will likely visit the clinic. If the medical condition of the patient with the implanted device warrants a continuous monitoring or adjustment of the device, the patient will have to stay in the hospital for an extended period of time. Such continuous treatment plans pose both economic and social hardship on patients. Depending on the frequency of data collection this procedure may seriously inconvenience patients that live in rural areas or have limited physical mobility. The need for upgrading the software of an implanted medical device also requires another trip to the hospital to have the upgrade installed. Further, as the segment of the population with implanted medical devices increases many more hospitals, clinics and service personnel will be needed to provide in-hospital care to patients, thus escalating the cost of healthcare.

Updating operating parameters and upgrading software in an implanted device are two examples where the state of an implanted device is changed. If the process of changing the state of an implanted device is interrupted, the physician must restore the device to a known state to ensure proper operability. If state changes to an implanted device are directed from a remote location, the process must also address possible interruptions.

SUMMARY OF THE INVENTION

Various embodiments of the present invention are directed to addressing various needs in connection with programming an IMD. Accordingly, the present invention provides a method and system that reduces the risk of leaving an IMD in an undesirable state when conditions unexpectedly change during programming of the IMD.

In various embodiments the present invention supports a communications system for transferring information between an IMD and a remote expert data center capable of dispensing therapy and clinical care on real-time basis. The present invention provides a method that improves the degree of patient safety while providing access to a remote expert data system. The capability provided by the present invention reduces the burden of the IMD patient of having to travel to a specific hospital or clinic for program upgrades, physician follow up evaluations and adjustments that need to be made to the IMD(s).

According to one embodiment of the invention, failure mode recovery in an implanted device is facilitated when a communications link with a medical communications system having an application program is interrupted. The method includes establishing a communications link between the medical communications system and an extender module configured to receive an application proxy from the application program. The application proxy, which is configured to transition the implanted device to a recovery state in response to a set of conditions, is then loaded into the extender module via the application program. The application program then transitions the implanted device to a completed state, and the transition process is monitored. The implanted device is automatically restored by the application proxy to the recovery state if the set of conditions is detected while transitioning to the completed state.

According to another embodiment of the invention, failure mode recovery in an implanted device is facilitated when a communications link with a medical communications system is interrupted. The method includes loading the application proxy from the application program into the extender module. The application proxy is configured to transition the implanted device to a recovery state in response to a set of conditions. A communications link is then established between the implanted device and the medical communications system via the extender module. The implanted device then transitions to a completed state via the application program, while the transition to the completed state is monitored. The implanted device is automatically restored by the application proxy to the recovery state if the set of conditions is detected while transitioning to the completed state.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a method and system for conducting failure mode recovery of an IMD that encounters an interruption in IMD programming that would leave the IMD in an undesirable state. While the present invention is not necessarily limited to such an application, the invention will be better appreciated using a discussion of example embodiments in such a specific context.

Figure 1:
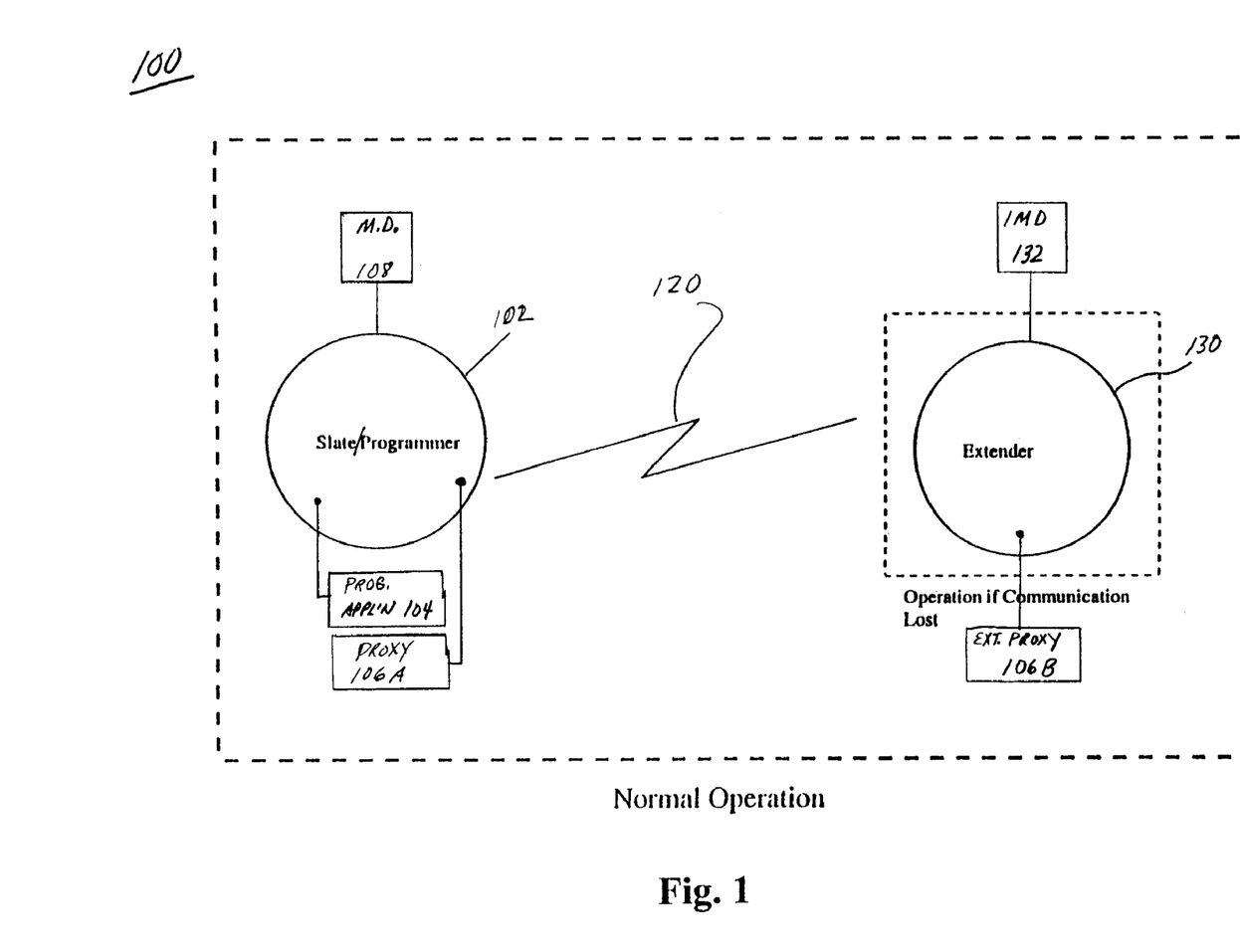
FIG. 1 illustrates a block diagram of an IMD programming and failure recovery mode system in accordance with an example embodiment of the invention.

Referring now to the figures, FIG. 1 illustrates a block diagram of an IMD programming and failure recovery mode system 100 in accordance with an example embodiment of the invention. System 100 includes a programmer or programming unit 102, that is part of a medical communications system, having a programmer application 104 and an application extender proxy program 106A. Programmer 102 is used by a physician 108 (or any other medical professional) to communicate with and program an IMD 132. System 100 also includes an extender module 130, communicatively coupled via communications link 120 to programmer 102, which interfaces more directly with IMD 132. Extender module 130 includes a processor and memory arrangement configured to provide failure mode recovery capabilities upon receiving the application extender proxy program 106A, which is designated as 106B when loaded into extender module 130. In one example, a patient with IMD 132 is remote from a hospital or clinic but is in need of an IMD evaluation or programming. With the present invention, extender module 130 extends the programming capabilities of programmer 102 to the patient, with control of the programming being directed from the facility where the physician is located. An interruption in programming may leave IMD 132 in an unknown state that may endanger the patient. With the aid of application proxy 106B, any interruption in communications or changes in programming conditions will allow system 100 to recover the IMD to a normal operating state. The failure mode recovery is transparent to the patient.

Figure 2:
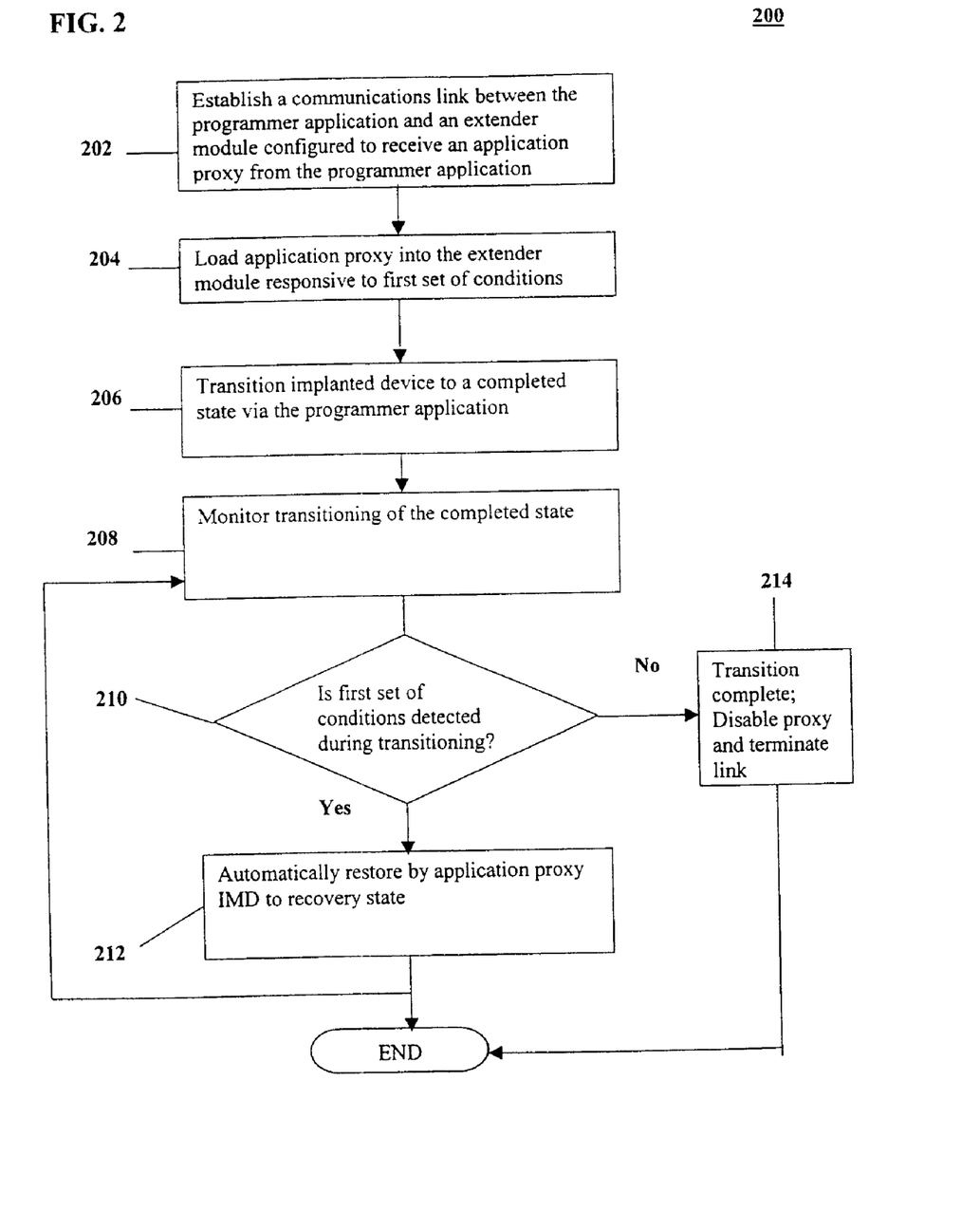
FIG. 2 is a flowchart illustrating the manner of configuring an IMD programming system for conducting failure mode recovery of an IMD when programming is interrupted in accordance with an example embodiment of the invention.

Referring now to FIG. 2, a flowchart 200 illustrates an example process for returning an IMD to a known operating state when IMD programming is interrupted (or when certain conditions occur) in accordance with an example embodiment of the invention. The method of the present invention facilitates failure mode recovery of an implanted device when a communications link with a medical communications system having a programmer application program is interrupted. Flowchart 200 is an example description of at least a single programming of device transition; however the IMD device may move through several transitions before the programming session is complete. At step 202, a communications link is first established between the medical communications system, which includes programmer 102, and extender module 130 that is configured to receive an application proxy 106A from the application program 104. At step 204, application proxy 106A is loaded into extender module 130 via application program 104. The application proxy 106A is configured to transition implanted device 132 to a recovery state in response to a set of conditions. The set of conditions include, but are not limited to, interruption in the communications link between the medical communications system and extender module 130; misalignment of the programming head of the extender module in detecting ECG readings or in conducting telemetry with the IMD; loss of telemetry connection with the IMD; a failure of programmer 102; poor placement of the programming head proximate the IMD and the patient's heart; and a poor connection between the extender module and the programming unit.

At this point, the extender performs the programming function proximate to the patient even though the actual programming unit may be remotely located from the patient. When the extender is in communication with the programming unit, the normal programming session can commence. At step 206, implanted device 132 transitions to a completed state under control of the programmer application program. In one example, transitioning to a completed state includes opening the read switch, programming and closing the read switch, thereby returning the IMD to its normal operating state. At the programmer during programming, a physician or healthcare specialist provides remote analysis of the data and approves changes in therapy, for example. At step 208, the transition to the completed state is monitored for various conditions. A communications interruption between the IMD and the programmer during a state transition could leave the IMD in an unstable state, thereby endangering the patient. In addition, stray radio frequency signals or electroread switchic waves can disrupt programming of the IMD also leaving the IMD in an unstable state. In view of the foregoing, at step 210 a determination is made whether a set of conditions has been detected during the transition to the completed state. If so, at step 212 the implanted device is automatically restored by the application proxy 106B to a known, stable state. Restoring the IMD to the stable state includes, for example, backing out of a programming mode or cease performing upgrades. The process can end after step 212 or can return to monitoring step 208 to monitor any additional state transitions prompted by additional programming efforts after communications have been re-established. In order to re-establish communications with the IMD and resume the programming session, the application proxy would need to be downloaded or pre-loaded into the extender again.

With reference to step 210, if the set of conditions is not detected during the transition, then the transition to the completed state continues until completion. Once transition is complete the IMD is ready for the next transition. Where additional state transitions (or programming) are not expected and a message is sent from programmer 102 to the extender module 130, at step 214, to disable application proxy 106B and to terminate communications link 120.

In another embodiment, the extender module is the programming head of programmer 102 that is communicatively coupled to programmer 102. Prior to collecting ECG data and coupling the programmer with the IMD, the application proxy is downloaded automatically into the memory of the extender module. Since the extender module has a processor and a memory circuit arrangement, it is capable of receiving and storing the application proxy. If during the programming session with the patient, programmer 102 crashes or becomes disabled, the extender module is capable of automatically restoring the IMD to a known state. The extender module also includes a link electronics module (LEM, FIG. 3) that senses whether communications have been lost with programmer 102. Prior systems required that the application proxy be manually loaded into the extender module (programming head) and that the application proxy or emergency programming be initialized by actuating a button on the programming head by the medical professional. One of the advantages to the present system is that the application proxy with the emergency programming is automatically pre-loaded at programmer start-up and the application proxy automatically restores the IMD to the recovery state upon the LEM sensing an interruption in communications from the programmer.

Figure 3:
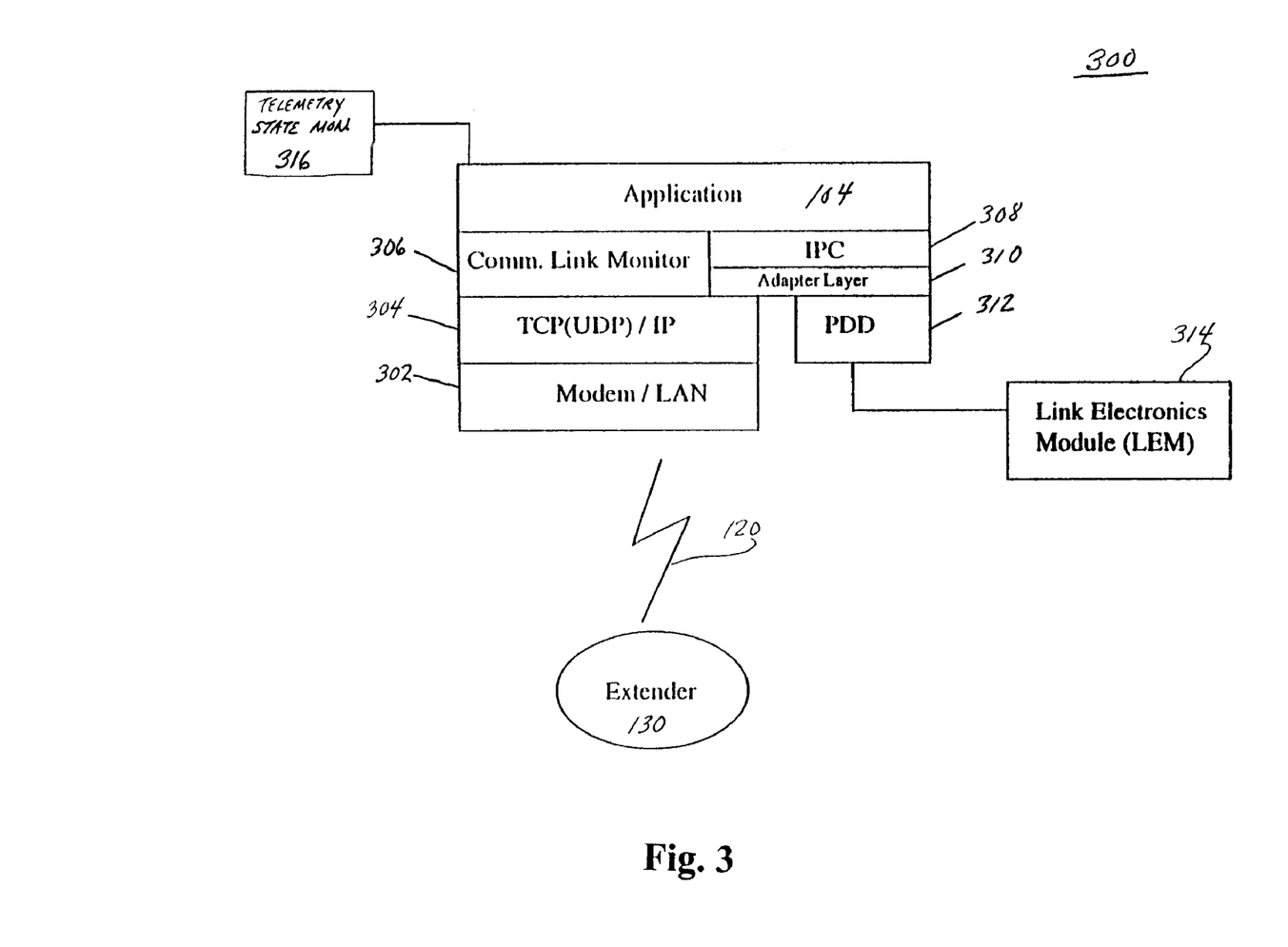
FIG. 3 is a block diagram of an example programming unit of the IMD programming and failure recovery mode system in accordance with an example embodiment of the invention.

Referring now to FIG. 3, a block diagram 300 illustrates an example programming unit 102 of the IMD programming and failure mode recovery system 100 in accordance with an example embodiment of the invention. Extender module 130 is coupled to programming unit 102 via communications link 120, which include, for example, a local area network, wide area network, and a public service telecommunications network (wired and wireless). A link can also be provided to the Internet via a PC or a wireless link to a global satellite communications network. A more detailed discussion of the methods of communicating remotely with an IMD is provided in U.S. Pat. No. 5,752,976 to Duffin et al, which is assigned to the assignee of the present invention and is incorporated herein by reference.

Programming unit 102, in this example embodiment, includes a modem/LAN module 302 coupled to a TCP (UDP)/IP module 304 for communications with various networks. A communications link monitor (CLM) 306 that monitors the integrity of the communications link with extender module 130 is coupled to module 304 and to programmer application 104. In particular, CLM 306 monitors the state of connection with the extender, generates events to application 104 that include notification of availability of voice communications after communications link is interrupted, and generates a message for display of an expected application proxy response to a particular event or condition that occurs. CLM 306 also provides the following functions: validating the modem connection to the programmer/information network to ensure that there is sufficient data throughput; and enabling feature availability on the programmer and information network, such as ECG data, uplink telemetry waveform data, non-hazardous downlink data (e.g., diagnostics, interrogations) and hazardous downlink data (e.g., disable tachycardia detection). CLM 306 also validates initialization steps (e.g., connected to IN, patient is monitored, ready to begin session) and monitors communications on the programming side of system 100 continuously. An IPC (Interprocessor Communications) module 308 is coupled to application 104 and communicates with the link electronics module 314 of the programmer through PDD 312 (peripheral device driver) or alternatively communicates with extender module 130 through TCP/EP module 304 and modem 302. An adapter layer 310 is interposed between IPC 308 and PDD 312 and serves as an intermediary between the two modules in directing data to either a local LEM 314 or to the remote extender module 130. A telemetry state monitor 316 is also coupled to programmer application 104 for monitoring telemetry waveforms that are generated by the IMD. Any irregularities are immediately reported to application 104. The telemetry state monitor also sends status messages to the extender and to the programmer and determines the status of the IMD read switch.

Figure 4:
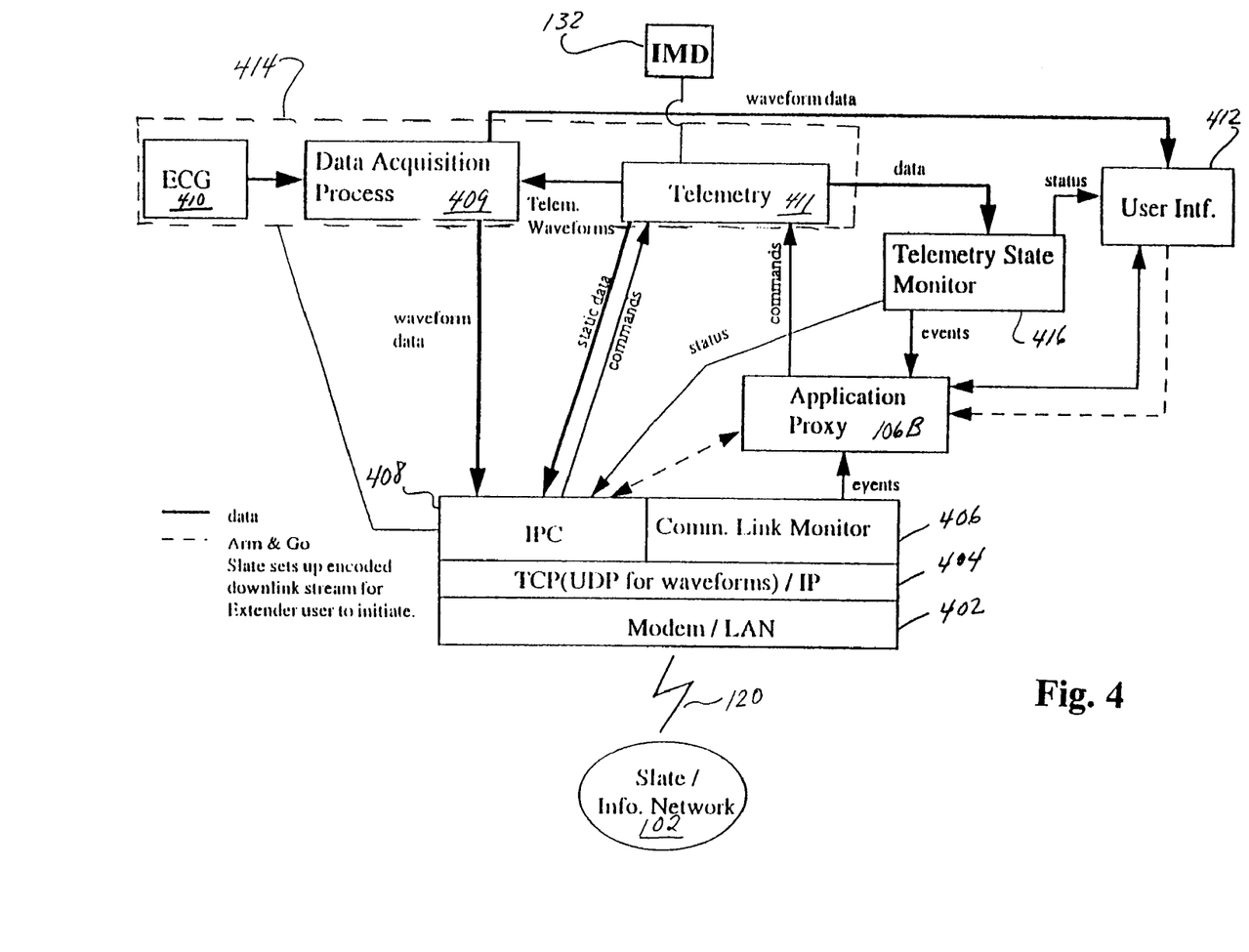
FIG. 4 is a block diagram of an example of an extender module of the IMD programming and failure recovery mode system in accordance with an example embodiment of the invention.

Referring now to FIG. 4, a block diagram 400 illustrates an example of an extender module 130 side of the IMD programming system 100 in accordance with an example embodiment of the invention. As shown, programming unit 102 is coupled to extender module 130 via communications link 120. Extender module 130 includes a modem/LAN module 402 coupled to a TCP(UDP)/IP module 404 for communications with various networks and a communications link monitor (CLM) 406 that monitors the integrity of the communications link between programmer 102 and extender module 130. CLM 406 provides similar functions to the extender module as CLM 306 provides to the programmer. In addition, CLM 406 advises proxy 106B when there is a communications breakdown or when another condition has occurred that requires enabling the application proxy.

An IPC module 408 is coupled to application proxy 106B and communicates with the link electronics module (LEM) 414. LEM 414 includes a data acquisition process module 409, an ECG module 410 and a telemetry module 411. In this example, IMD 132 is coupled to the telemetry module 411 that sends telemetry waveforms that are generated by the IMD to the telemetry state monitor 416 and to the data acquisition process module (DAP) 409. DAP module 409 also gathers ECG waveform data via ECG module 410 from the patient having IMD 132. DAP 409 proceeds to link the telemetry data from the IMD with the ECG data and then bundles the data for transmission in regular intervals back to programming unit 102. Programming unit 102 receives and displays the data to the physician and to the user via a user interface 412 (through extender 130). User interface 412 provides regular status updates to the medical personnel using the extender to re-position the programming head or is used to display messages coming from the application proxy (e.g., cancel read switch) if a communications breakdown occurs. In an example embodiment, the user interface is used to input data or commands to the application proxy.

The telemetry state monitor (TSM) 416 is coupled to application proxy 106B and monitors telemetry waveforms that are generated by the IMD. In addition, the telemetry state monitor regularly samples waveform data from the IMD to determine if the telemetry link is still valid and determines the status of the read switch. The TSM then decides whether it is necessary to notify the application proxy 106B that a condition of concern has occurred or if any irregularities are identified. The TSM also sends status messages to extender 130, user interface 412 and to programmer 102.

In addition, IPC 408 sends commands to telemetry module 411 coming from the programmer and receives static data from telemetry module 411 that is sent to the programmer along with status data from telemetry state monitor 416. IPC 408 also serves as an intermediary in directing data to either LEM 414 or to the extender module 130. Application proxy 106B provides the following functions that can be grouped together in different ways depending on the conditions that are being responded to. The application proxy acts on behalf of the programming application (or programmer) to respond to unexpected events that may occur in programming an IMD and implements certain downlink transmission commands, such as canceling read switch, performing emergency programming, canceling temporary settings and storing last known permanent values. The application proxy also maps events to the downlink transmissions; coordinates device interactions with the programming application; and notifies the user interface (UI) of changes in communications status with the actions to be taken in connection with the changes. I In another related application, the present invention is useful in training medical personnel in remote locations on the aspects of programming IMDs. A voice communications link would first be established with an IMD operator, located proximate the patient with the IMD to be interrogated, that will be moving the programming head or wand coupled to the extender module. If the communications link with the extender module is interrupted, the IMD operator is advised by immediately over the voice communications link the status of the programming during the training session by the training physician located at the programming location. The voice communications link can be established via a telephone, a video conference call, a cellular telephone, via a separate Internet connection or other related communications formats.

Some of the advantages provided by the various embodiments of the present invention include enhanced patient availability for regular IMD and ECG evaluations; increased accuracy of data being communicated between the implanted device and the medical communications system due to the monitoring of the telemetry link with the implanted device. In addition, the present invention provides for a comfortable programming or interrogation session in a patient's home or familiar environment and eliminates the necessity of traveling to the hospital.

The present invention is compatible with a number of techniques for interrogating and programming implanted medical devices, such as drug pumps, neurological implants, nerve stimulators, various cardiac implants and equivalent medical devices. In addition, the embodiments described are compatible with remote patient management systems that interact with remote data and expert data centers and compatible with a data communication system that enables the transfer of clinical data from the patient to a remote location for evaluation, analysis, data reposition, and clinical evaluation.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A method for conducting failure mode recovery in an implantable medical device upon interruption of communications with the implantable medical device, the method comprising:
   (a) establishing a communications link between a remote medical communications system having a programming application program and a programming extender module configured to receive an application proxy from the application program;
   (b) loading the application proxy into the programming extender module;
   (c) transitioning the implantable medical device to a known recovery state in response to an interruption of a communications with the implantable medical device;
   (d) transitioning the implantable medical device to a predetermined completed state;
   (e) monitoring transition of the implantable medical device to the predetermined completed state; and
   (f) automatically restoring the implantable medical device to the known recovery state by the application proxy if an interruption of communications with the implantable medical device is detected while transitioning to the completed state.

2. The method of claim 1, further comprising the step of automatically re-establishing the communications link with the implantable medical device by repeating steps (a) and (b) after an interruption of communications with the implantable medical device has been detected.

3. The method of claim 2, further comprising the step of establishing a voice communications link with a patient having the implantable medical device at the programming extender module before step (a).

4. The method of claim 1, wherein the restoring step includes the steps of:
   performing downlink transmission commands that transition the implanted device out of a programming mode;
   monitoring the communications link for changes in status; and
   reporting changes in status of the communications link via a user Interface.

5. The method of claim 4, further comprising the step of displaying messages via the user interface on actions performed by the application proxy.

6. The method of claim 4, further comprising the step of reconfiguring the application proxy via the user interface.

7. The method of claim 1, wherein the monitoring step includes the steps of:
   validating a communications connection with the remote medical communications system;
   validating a set of initialization steps for programming the implantable medical device; and
   monitoring the communications link between the implantable medical device and the remote medical communications system.

8. The method of claim 1, wherein step (e) includes collecting a set of ECG and telemetry waveform data as a data set and transmitting the data set to the remote medical communications system.

9. The method of claim 8, wherein collecting telemetry waveform data includes sampling data to validate integrity of a telemetry communications link.

10. The method of claim 9, further comprising the step of transmitting a telemetry communications link status code to the application program and to the extender module.

11. The method of claim 1, further comprising the step of disabling the application proxy and terminating the communications link when an interruption of communications with the implantable medical device is not detected after step (e).

12. A system for conducting failure mode recovery in an implantable medical device upon interruption of with the implanted medical device, the system comprising:
 (a) a remote medical communications system having an implantable medical device programming application program;
 (b) a programming extender module interfacing the medical communications system to the implantable medical device and being, configured to receive an application proxy from the application program;
 (c) means for establishing a communications link between the medical communications system and the programming extender module;
 (d) means for loading an application proxy into the: programming extender module and transitioning the implantable medical device to a known recovery state in response to an interruption in communications between the medical communications system and the implantable medical device;
 (e) means for transitioning the implantable medical device to a predetermined completed state;
 (f) means for monitoring transition of the implantable medical device to the completed state; and
 (g) the application proxy being configured to automatically restore the implantable medical device to the recovery state when an interruption in communications between the medical communications system and the implantable medical device is detected while the implantable medical device is transitioning to the completed state.

13. A method for collecting waveform data from a patient's heart, the method comprising:
 (a) establishing a communications link between a remote medical communications system having an application program and an extender module configured to receive an application proxy from the application program;
 (b) loading the application proxy into the extender module via the application program, the extender module being proximate the patient's heart, the application proxy being configured to execute the application program and to re-establish the communications link in response to a loss of communications;
 (c) collecting waveform data from the patient's heart; and
 (d) monitoring the communications link between the remote medical communications system and the extender module for a loss of communications and advising the application proxy if a loss of communications is detected.

14. A system for collecting waveform data from a patient's heart, the system comprising:
 (a) a remote medical communications system having an implantable medical device programming application program;
 (b) a programming extender module interfacing the medical communications system to the implantable medical device and being configured to receive an application proxy from the application program, the programming extender module being located proximate the patient's heart;
 (c) means for establishing a communications link between the medical communications system and the programming extender module;
 (d) means for loading the application proxy into the programming extender module to re-establish an interrupted communications link;
 (e) means for collecting waveform data from the patient's heart; and
 (f) means for monitoring the communications link between the medical communications system and the programming extender module and advising the application proxy if an interruption of the communications link is detected.

15. A method for conducting failure mode recovery in an implantable medical device upon loss of communications with a remote medical communications system, the method comprising:
 (a) loading an application proxy from a programming application program resident on the remote medical communications system into a programming extender module, the application proxy being configured to transition the implantable medical device to a known recovery state in response to a loss of communications;
 (b) establishing a communications link between the implantable medical device and the remote medical communications system via the programming extender module;
 (c) transitioning the implantable medical device to a completed state via the programming application program;
 (d) monitoring transition of the implantable medical device to the completed state; and
 (e) automatically restoring the implantable medical device to the known recovery state by the application proxy if a loss of communications is detected while transitioning the implantable medical device to the completed state.

16. The method of claim 15, wherein the restoring step includes the steps of implementing downlink transmission commands; monitoring the communications link for changes in status; and reporting changes in the communications link status via a user interface.

17. The method of claim 16, wherein the restoring step further includes the steps of mapping events to downlink transmissions and coordinating implantable medical device interactions with the application program.

18. The method of claim 15, wherein the monitoring step includes the step of monitoring the communications link between the implantable medical device and the remote medical communications system.

19. A system for conducting failure mode recovery in an implantable medical device upon loss of communications with a remote medical communications system having an application program for programming the implantable medical device, the system comprising:
 (a) a programming extender module interfacing the implantable medical device with the remote medical communications system;
 (b) means for loading an application proxy from the application program into the programming extender module, the application proxy configured to transition the implanted device to a known recovery state in response to a loss of communications;
 (c) means for establishing a communications link between the implantable medical device and the medical communications system via the extender module after a loss of communications;

(d) means for transitioning the implantable medical device to a completed state via the application program;

(e) means for monitoring transition of the implantable medical device to the completed state; and (f) means for automatically restoring the implantable medical device to the known recovery state if a loss of communications is detected while the implantable medical device is transitioning to the completed state.

20. A method for conducting failure mode recovery in an implantable medical device upon loss of communications with a remote medical communications system, the method comprising:

(a) establishing a first communications link between the remote medical communications system and an extender module;

(b) loading an application proxy from a programming application program resident on the remote medical communications system into the extender module, the application proxy being configured to transition the implantable medical device to a known recovery state in response to a loss of communications;

(c) establishing a second communications link between the implantable medical device and the remote medical communications system via the extender module;

(d) transitioning the implantable medical device to a completed state via the application program;

(e) monitoring transition of the implantable medical device to the completed state; and (f) automatically restoring the implantable medical device to the known recovery state by the application proxy if a loss of communications is detected while transitioning the implantable medical device to the completed state.

21. The method of claim 20, wherein the restoring step includes the steps of implementing downlink transmission commands; monitoring the communications link for changes in status; and reporting changes in the communications link status via a user interface.

22. The method of claim 20, wherein the restoring step further includes the steps of mapping events to downlink transmissions and coordinating implantable medical device interactions with the application program.

23. The method of claim 20, wherein the monitoring step includes the step of monitoring the communications link between the implantable medical device and the remote medical communications system.

24. A system for conducting failure mode recovery in an implantable medical device upon loss of communications with a remote medical communications system, the system comprising:

(a) a programming extender module;

(b) means for establishing a first communications link between the remote medical communications system and the programming extender module;

(c) means for loading a application proxy from a programming application program resident on the remote medical communications system into the programming extender module, the application proxy being configured to transition the implantable medical device to a known recovery state in response to a loss of communications;

(d) means for establishing a second communications link between the implantable medical device and the remote medical communications system via the programming extender module;

(e) means for transitioning the implantable medical device to a completed state via the application program;

(f) means for monitoring transition of the implantable medical device to the completed state; and (g) an application proxy configured to automatically restore the implantable medical device to the known recovery state if a loss of communications is detected while transitioning the implantable medical device to the completed state.

* * * * *